United States Patent [19]
Agricola et al.

[11] 3,959,458
[45] May 25, 1976

[54] ORAL COMPOSITIONS FOR CALCULUS RETARDATION

[75] Inventors: Francis Oswald Agricola; William Watson Briner; Robert James Granger; James Stone Widder, all of Springfield Township, Hamilton County, Ohio

[73] Assignee: The Procter & Gamble Company, Cincinnati, Ohio

[22] Filed: Aug. 30, 1974

[21] Appl. No.: 501,909

Related U.S. Application Data

[63] Continuation-in-part of Ser. No. 329,783, Feb. 9, 1973, abandoned, which is a continuation-in-part of Ser. No. 223,353, Feb. 3, 1972, abandoned, which is a continuation-in-part of Ser. No. 106,921, Jan. 20, 1971, abandoned.

[52] U.S. Cl.................................. 424/52; 424/57
[51] Int. Cl.².............................................. A61K 7/18
[58] Field of Search................................ 424/49–52, 424/54

[56] References Cited
UNITED STATES PATENTS

| | | | |
|---|---|---|---|
| 3,538,230 | 11/1970 | Pader et al............................ | 424/50 |
| 3,608,067 | 9/1971 | Irani..................................... | 424/52 |
| 3,678,154 | 7/1972 | Widder et al.......................... | 424/52 |

Primary Examiner—Shep K. Rose
Attorney, Agent, or Firm—Ronald L. Hemingway; Robert B. Aylor; George W. Allen

[57] ABSTRACT

Oral compositions, such as toothpaste, mouthwash, and the like, containing certain anticalculus agents, and a specific anticaries agent which provides anticaries benefits while avoiding adverse effects on silicate filling materials present in the mouth.

17 Claims, No Drawings

ORAL COMPOSITIONS FOR CALCULUS RETARDATION

CROSS-REFERENCE TO RELATED APPLICATIONS

This application is a continuation-in-part of application Ser. No. 329,783, filed Feb. 9, 1973 (now abandoned), which in turn is a continuation-in-part of application Ser. No. 223,353, filed Feb. 3, 1972 (now abandoned), which in turn is a continuation-in-part of application Ser. No. 106,921, filed Jan. 20, 1971 (now abandoned).

THE PRIOR ART

U.S. Pat. No. 3,678,154, issued July 18, 1972, to Widder et al., discloses dentifrices containing certain polyphosphonates and fluorides. U.S. Pat. No. 3,608,067, issued Sept. 21, 1971, to R. R. Irani, discloses certain insoluble phosphonate salts as abrasives in dentifrices which contain monofluorophosphate salts. U.S. Pat. No. 3,538,230, issued Nov. 3, 1970, to M. Pader et al., discloses dentifrices containing xerogel abrasives and monofluorophosphate salts. British Pat. No. 1,232,889, published May 19, 1971, discloses dentifrice compositions containing certain tris(phosphonoalkyl) amines and sources of fluorine such as fluorides and sodium monofluorophosphate.

BACKGROUND OF THE INVENTION

The field of this invention is "oral compositions" which term is used herein to designate products which in the ordinary course of usage are retained in the oral cavity for a time and in a manner sufficient to contact substantially all of the dental surfaces, but are not intentionally ingested. Such products include, for example, dentifrices, mouthwashes, prophylaxis pastes and topical solutions.

Safe and effective oral compositions for calculus inhibition have been disclosed in U.S. Pat. No. 3,678,154 of James S. Widder and William W. Briner for "ORAL COMPOSITIONS FOR CALCULUS RETARDATION", issued July 18, 1972, and in a series of applications by William W. Briner and James S. Widder as follows: Ser. No. 828,842, filed Oct. 21, 1970; Ser. No. 89,069, filed Nov. 12, 1970 and Ser. No. 89,070, filed Nov. 12, 1970; all of said applications being for "ORAL COMPOSITIONS FOR CALCULUS RETARDATION", and all of said applications being abandoned. All of said applications and said patent are incorporated herein by reference.

SUMMARY OF THE INVENTION

It has now been discovered that if a particular anticaries agent, i.e., sodium or calcium monofluorophosphate, is used in combination with the anticalculus agents of the applications disclosed hereinbefore or the condensation products of ammonia and phosphorus pentoxide, there is no detectable damage to silicate fillings in the mouth under conditions of ordinary use, whereas adverse effects can be detected when other anticaries agents, e.g., sodium fluoride, are used.

DETAILED DESCRIPTION OF THE INVENTION

This invention is an oral composition effective in inhibiting the formation of dental calculus and caries without adversely affecting the tooth structure comprising (1) from about 0.01% to about 10% by weight of an anticalculus agent selected from the group consisting of those of the formulae:

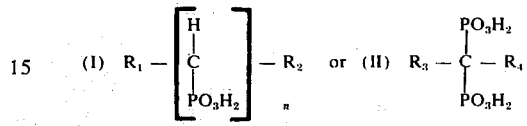

wherein $R_1$ and $R_2$ are either hydrogen or $CH_2OH$; $n$ is an integer of from 3 to 10; $R_3$ is either hydrogen, an alkyl group containing from 1 to about 20 carbon atoms, an alkenyl group containing from 2 to about 20 carbon atoms, an aryl group (e.g., phenyl and naphthyl), a phenylethenyl group, a benzyl group, a halogen atom (e.g., chlorine, bromine, and fluorine), an amine group, a substituted amino group (e.g., dimethylamino, diethylamino, N-hydroxy-N-ethylamino, acetylamino), $-CH_2COOH$, $-CH_2PO_3H_2$, $-CH(PO_3H_2)(OH)$ or $-CH_2CH(PO_3H_2)_2$; $R_4$ is either hydrogen, a lower alkyl group (e.g., methyl, ethyl, propyl, and butyl), an amino group, a benzyl group, a halogen atom (e.g., chlorine, bromine and fluorine), a hydroxyl group, $-CH_2COOH$, $-CH_2PO_3H_2$, or $-CH_2CH_2PO_3H_2$;

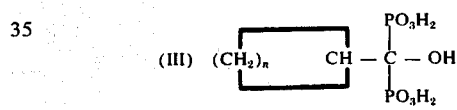

wherein $n$ is an integer from 3 to 9;

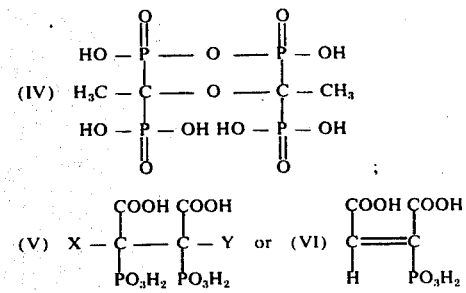

wherein X and Y are each either hydrogen or a hydroxy group; and the alkali metal (e.g., sodium and potassium), ammonium and low molecular weight substituted ammonium (e.g., mono-, di-, and triethanolammonium) salts of the foregoing compounds; or the condensation products of ammonia and phosphorus pentoxide, e.g.,

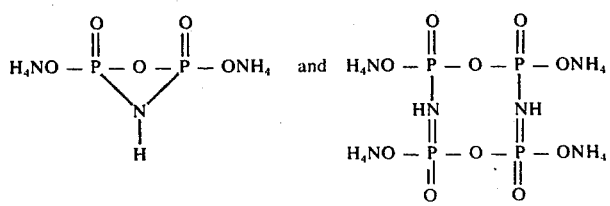

and (2) from about 0.2% to about 8% by weight of an orally acceptable monofluorophosphate, the pH of the composition being within the range from about 5.0 to about 11.0.

Operable polyphosphonates of the above formula (I) include propane-1,2,3-triphosphonic acid; butane-1,2,3,4-tetraphosphonic acid; hexane-1,2,3,4,5,6-hexaphosphonic acid; hexane-1-hydroxy-2,3,4,5,6-pentaphosphonic acid; hexane-1,6-dihydroxy-2,3,4,5-tetraphosphonic acid; pentane-1,2,3,4,5-pentaphosphonic acid; heptane-1,2,3,4,5,6,7-heptaphosphonic acid; octane-1,2,3,4,5,6,7,8-octaphosphonic acid; nonane-1,2,3,4,5,6,7,8,9-nonaphosphonic acid; decane-1,2,3,4,5,6,7,8,9,10-decaphosphonic acid; and the alkali metal ammonium and low molecular weight substituted ammonium salts of these acids, e.g., sodium, potassium, ammonium, triethanolammonium, diethanolammonium, and monoethanolammonium salts.

Propane-1,2,3-triphosphonic acid and salts thereof can be prepared by a process disclosed in the patent of D. Allan Nicholson et al., U.S. Pat. No. 3,743,688, issued July 3, 1973.

Butane-1,2,3,4-tetraphosphonic acid and salts thereof can be prepared by a process disclosed in the patent of D. Allan Nicholson et al., U.S. Pat. No. 3,755,504, issued Aug. 28, 1973.

The higher aliphatic vicinal polyphosphonates and salts thereof can be prepared by the process disclosed in U.S. Pat. No. 3,584,035, of D. Allan Nicholson and Darrel Campbell, issued June 8, 1971.

Among the operable polyphosphonates encompassed by the above formula (II) are ethane-1-hydroxy-1,1-diphosphonic acid; methanediphosphonic acid; methanehydroxydiphosphonic acid; ethane-1,1,2-triphosphonic acid; propane-1,1,3,3-tetraphosphonic acid; ethane-2-phenyl-1,1-diphosphonic acid; ethane-2-naphthyl-1,1-diphosphonic acid; methanephenyldiphosphonic acid; ethane-1-amino-1,1-diphosphonic acid; methanedichlorodiphosphonic acid; nonane-5,5-diphosphonic acid, n-pentane-1,1-diphosphonic acid; methanedifluorodiphosphonic acid methanedibromodiphosphonic acid; propane-2,2-diphosphonic acid; ethane-2-carboxy-1,1-diphosphonic acid; propane-1-hydroxy-1,1,3-triphosphonic acid; ethane-2-hydroxy-1,1,2-triphosphonic acid; ethane-1-hydroxy-1,1,2-triphosphonic acid; propane-1,3-diphenyl-2,2-diphosphonic acid; nonane-1,1-diphosphonic acid; hexadecane-1,1-diphosphonic acid; pent-4-ene-1-hydroxy-1,1-diphosphonic acid; octadec-9-ene-1-hydroxy-1,1-diphosphonic acid; 3-phenyl-1,1-diphosphonoprop-2-ene; octane-1,1-diphosphonic acid; dodecane-1,1-diphosphonic acid; phenylaminomethanediphosphonic acid; naphthylaminomethanediphosphonic acid; N,N-dimethylaminomethanediphosphonic acid; N-(2-hydroxyethyl)-aminomethanediphosphonic acid; N-acetylaminomethanediphosphonic acid; aminomethanediphosphonic acid; and the alkali metal, ammonium and low molecular weight substituted ammonium salts of these acids, e.g., sodium, potassium, ammonium, triethanolammonium, diethanolammonium and monoethanolammonium salts.

Examples of compounds coming within the formula (III) include the following: Methanecyclobutylhydroxydiphosphonic acid; methanecyclopentylhydroxydiphosphonic acid; methanecyclohexylhydroxydiphosphonic acid; methanecycloheptylhydroxydiphosphonic acid; methanecyclooctylhydroxydiphosphonic acid; methanecyclononylhydroxydiphosphonic acid; methanecyclodecylhydroxydiphosphonic acid.

Each of the sodium, potassium, ammonium, monoethanolammonium, diethanolammonium and triethanolammonium salts of the above recited methanecycloalkylhydroxydiphosphonic acids can be used in the practice of the present invention.

Especially preferred methanecycloalkylhydroxydiphosphonates for the purpose of this invention are methanecyclopentylhydroxydiphosphonic acid, methanecyclohexylhydroxydiphosphonic acid, methanecycloheptylhydroxydiphosphonic acid and the aforementioned salts of these acids.

Examples of cyclic tetraphosphonic acids [Formula (IV)] include the alkali metal salts (e.g., sodium and potassium), ammonium salts and low molecular weight substituted ammonium salts (e.g., mono-, di-, and triethanolammonium) of the subject compounds.

Operable carboxyphosphonates of the above formula (V) include ethane-1,2-dicarboxy-1,2-diphosphonic acid; ethane-1,2-dicarboxy-1,2-dihydroxy-1,2-diphosphonic acid; ethane-1,2-dicarboxy-1-hydroxy-1,2-diphosphonic acid; and salts of these acids, e.g., sodium, potassium, ammonium, triethanolammonium, diethanolammonium, and monoethanolammonium salts.

Among the operable carboxyphosphonates encompassed by the above formula (VI) are ethene-1,2-dicarboxy-1-phosphonic acid; and the salts of this acid, e.g., sodium, potassium, ammonium, triethanolammonium, diethanolammonium, and monoethanolammonium salts. While the above formula (VI) is representative of cis-isomers, the corresponding trans-isomers are also useful herein. Reference hereinafter to ethene-1,2-dicarboxy-1-phosphonic acid or salts thereof, unless otherwise specified, is intended as comtemplating the cis- and trans-isomers and mixtures thereof.

Mixtures of any of the foregoing polyphosphonic acids and/or salts can be used in the compositions of this invention.

Ethane-1-hydroxy-1,1-diphosphonic acid, an especially preferred anticalculus agent, has the molecular formula $CH_3C(OH)(PO_3H_2)_2$. (According to nomenclature by radicals, the acid might also be named 1-hydroxyethylidene diphosphonic acid.) The most readily crystallizable salt of this acid is obtained when three of the acid hydrogens are replaced by sodium. Preferred salts for the purpose of this invention are the trisodium hydrogen salt which has the structure:

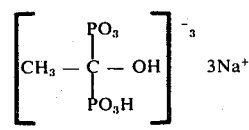

and the disodium salt.

The trisodium hydrogen salt normally crystallizes as the hexahydrate which loses some water during air-drying to yield a mixture of the hexa- and monohydrate averaging 3 to 4 molecules of water of hydration.

While any alkali metal, ammonium or low molecular weight substituted ammonium salt of ethane-1-hydroxy-1,1-diphosphonic acid can be used in the practice of this invention, the tetrasodium salt, the trisodium hydrogen salt, the disodium dihydrogen salt, the monosodium trihydrogen salt, and mixtures thereof are preferred. The other alkali metal, ammonium or low molecular weight substituted ammonium salts and mixtures thereof are also suitable. These compounds can be prepared by any suitable method, however, an especially preferred method is disclosed in U.S. Pat. No. 3,400,149, Quimby et al., issued Sept. 3, 1968.

The concentration of anticalculus agent in the oral compositions of this invention can range from about .01% to about 10% by weight. Oral compositions which in the ordinary course of usage could be accidentally ingested should contain lower concentration of anticalculus agent. Thus, a mouthwash in accordance with this invention preferably contains less than about 3% by weight of anticalculus agent. Dentifrice compositions, topical solutions and prophylaxis pastes, the latter to be administered professionally, can contain up to about 10% by weight, preferably from about 0.1% to about 5.0% by weight of anticalculus agent.

The compositions of this invention are characterized by containing an orally acceptable monofluorophosphate, preferably the sodium salt. Sodium monofluorophosphate is an effective anticaries agent which is unique in that unlike some water-soluble fluorides, it does not attack silicate filling materials when used in combination with the anticalculus agents described hereinbefore. Thus, if one desires to combine anticaries and anticalculus benefits without causing damage to silicate fillings, one must use the monofluorophosphate. The monofluorophosphate is preferably used in an amount which will provide an anticaries effect, i.e., in an amount of from about 0.2% to about 8%, preferably from about 0.5% to about 1.0% by weight.

In addition to the monofluorophosphate, it is possible to add a material which gives fluoride ions in water to increase the anticaries effectiveness of the compositions. So long as the level of free fluoride ion from this additional material is less than about 300 ppm, no appreciable silicate filling damage will occur.

Suitable water-soluble fluorides are disclosed in William W. Briner and James S. Widders' U.S. Pat. No. 3,535,421 issued Oct. 20, 1970, especially columns 3 and 4, and column 5, lines 1–24.

The pH of the compositions of this invention is preferably maintained within the range from about 5 to 11. Below about pH 5.0 certain of the anticalculus agents of this invention can damage dental enamel. Above about pH 11.0, oral irritation becomes excessive. A most preferred pH range is from about 6.0 to 7.5.

In addition to the essential components of the oral compositions of this invention as described in the foregoing, such compositions can also contain carriers suitable for use in the oral cavity. Such carriers include the usual components of toothpaste, toothpowder, mouthwash, prophylaxis pastes and the like as more fully described hereinafter.

A dentifrice, especially toothpaste, containing an anticalculus agent is a preferred embodiment of this invention. Toothpaste compositions conventionally contain abrasive materials, sudsing agents, binders, humectants, flavoring and sweetening agents.

Any conventional toothpaste abrasive can be used in the compositions of this invention. Thus, conventional abrasives such as dicalcium orthophosphate, calcium carbonate, and calcium pyrophosphate, including the $\beta$-phase calcium pyrophosphate prepared in accordance with the teachings of Schweizer, U.S. Pat. No. 3,112,247, granted Nov. 26, 1963, can be used. The $\beta$-phase calcium pyrophosphate is prepared by heating $\gamma$-phase calcium pyrophosphate to 700–900°C. to change at least 50% of the $\gamma$-phase to $\beta$-phase and then immediately cooling. Another class of abrasives for use herein are the particulate thermosetting polymerized resins as described by Cooley et al. in U.S. Pat. No. 3,070,510, granted Dec. 25, 1962. Suitable resins include, for example, melamines, phenolics, ureas, melamine-ureas, melamineformaldehydes, urea-formaldehydes, melamine-urea-formaldehydes, cross-linked epoxides, and cross-linked polyesters. Yet another type of abrasive for use herein is a silica xerogel abrasive having a surface area of at least 300 square meters per gram as disclosed in the copending divisional continuation-in-part application of William Watson Briner, Robert James Granger, and James Stone Widder. Ser. No. 437,280 for "ORAL COMPOSITIONS FOR CALCULUS RETARDATION" filed Jan. 28, 1974, which is a continuation-in-part of application Ser. No. 329,782, filed Feb. 9, 1973 (now abandoned), which in turn is a continuation-in-part of application Ser. No. 223,353, filed Feb. 3, 1972 (now abandoned), which in turn is a continuation-in-part of Ser. No. 106,921, filed Jan. 20, 1971 (now abandoned).

Other suitable abrasives include alumina, and the insoluble metaphosphates such as insoluble sodium metaphosphate (IMP). Mixtures of abrasives can also be used. In any case, the total amount of abrasive in the dentifrice embodiments of this invention can range from 0.5% to 95% by weight of the dentifrice. Preferably, toothpastes contain from 20% to 60% by weight of abrasive. Abrasive particle size preferably ranges rom $2\mu$ to $20\mu$.

The preferred abrasives are the $\beta$-phase calcium pyrophosphate of U.S. Patent 3,112,247; insoluble sodium metaphosphate; the resinous abrasives of U.S. Pat. No. 3,070,510; and the silica xerogel abrasives since they are more compatible with the anticalculus agents. Most preferred are the silica xerogels.

Suitable sudsing agents are those which are reasonably stable and form suds throughout a wide pH range, preferably non-soap anionic organic synthetic detergents. Examples of such agents are water-soluble salts of alkyl sulfate having from 10 to 18 carbon atoms in the alkyl radical, such as sodium lauryl sulfate, water-soluble salts of sulfonated monoglycerides of fatty acids having from 10 to 18 carbon atoms, such as sodium monoglyceride sulfonates; salts of $C_{10}$–$C_{18}$ fatty acid amides of taurine, such as sodium N-methyl-N-palmitoyl tauride; salts of $C_{10}$–$C_{18}$ fatty acid esters of isethionic acid; and subtantially saturated aliphatic acyl amides of saturated monoaminocarboxylic acids having 2 to 6 carbon atoms and in which the acyl radical contains 12 to 16 carbon atoms, such as sodium N-lauroyl sarcoside. Mixtures of two or more sudsing agents can be used.

The sudsing agent can be present in the dentifrice compositions of this invention in an amount from 0.5% to 5% by weight of the total compositions.

In preparing toothpastes, it is necessary to add some thickening material to provide a desirable consistency. Preferred thickening agents are hydroxyethyl cellulose and water-soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate, silica aerogels such as "Syloid 244", fumed silica such as "Cab-O-Sil", or other finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerine, sorbitol, and other edible polyhydric alcohols. The humectant can comprise up to about 36% by weight of the toothpaste composition.

Suitable flavoring agents include oil of wintergreen, oil of peppermint, oil of spearmint, oil of sassafras, and oil of clove. Sweetening agents which can be used include saccharin, dextrose, levulose and sodium cyclamate.

Several representative oral compositions illustrating this invention are set forth in the following examples.

EXAMPLE I

The following solutions were prepared and SS White MQ Silicate filling material chips were immersed in the solutions for two hours and five hours with the indicated observations of the chips:

(A) 1% disodium ethane-1-hydroxy-1,1-diphosphonate (EHDP);
(B) 333 ppm fluoride from sodium monofluorophosphate (MFP);
(C) 1% EHDP and 333 ppm MFP.

| Two Hour Exposure | Five Hour Exposure |
| --- | --- |
| (A) no change | very light roughening of surface detectable by touch only |
| (B) no change | very light whitening and very light roughening |
| (C) very light whitening | very light whitening and very light roughening |

Although most combinations of EHDP and other fluoride ion sources would severely attack the silicate filling materials, it appears that this combination damages the silicate filling materials in only a very small degree under the conditions of this test. When this combination is used in fully formulated dentifrices of the types specifically disclosed hereinafter, no damage to silicate fillings is detectable under conditions of normal use.

EXAMPLE II

A dentifrice is prepared having the following formula:

| Component | Percent by Weight |
| --- | --- |
| Sorbitol (70% aqueous solution) | 20.00 |
| Saccharin | 0.21 |
| EHDP | 3.00 |
| MFP | 0.76 |
| Veegum | 0.40 |
| Calcium pyrophosphate abrasive made according to the teaching of U.S. Pat. 3,112,247 | 39.00 |
| 5N.NaOH | 1.40 |
| Flavor | 1.00 |
| Sodium carboxymethylcellulose | 1.30 |
| Glycerine | 10.00 |
| Sodium coconut alkyl monoglyceride sulfonate | 0.75 |
| Sodium coconut alkyl sulfate | 3.12 |
| Distilled water | balance |

The pH, as made, is about 685 Silicate filling material, when exposed to the above formulation under conditions of ordinary use, does not show any detectable adverse effects.

EXAMPLE III

Yet another toothpaste is prepared in accordance with this invention, having the following composition:

| Component | Percent by Weight |
| --- | --- |
| Precipitated urea/formaldehyde condensate (abrasive) | 31.00 |
| Sorbitol (70% aqueous solution) | 6.25 |
| Glycerine | 18.00 |
| Sodium coconut alkyl sulfate | 0.40 |
| Sodium coconut monoglyceride sulfonate | 0.75 |
| Sodium carboxymethylcellulose | 1.15 |
| Magnesium aluminum silicates | 0.40 |
| Sodium saccharin | 0.12 |
| Flavoring | 0.95 |
| Methanediphosphonic acid | 1.50 |
| Sodium monofluorophosphate | 3.00 |
| Water | balance |
| Mole ratio polyphosphonate/fluoride 2.4 pH adjusted to 7.5 with 5N.NaOH | |

This composition is effective in retarding the formation of dental calculus when used in the conventional manner, and mature dental enamel and silicate fillings are not adversely affected thereby. The composition is effective in reducing the incidence of caries.

Several additional toothpastes are prepared having essentially the same composition as the toothpaste of Example III, but using the tetrasodium salt of ethane-1,1,2-triphosphonic acid; the pentasodium salt of propane-1-hydroxy-1,1,3-triphosphonic acid; the pentasodium salt of ethane-1-hydroxy-1,1,2-triphosphonic acid; the pentasodium salt of ethane-2-hydroxy-1,1,2-triphosphonic acid; ethane-2-naphthyl-1,1-diphosphonic acid; propane-1,2,3-triphosphonic acid; butane-1,2,3,4-tetraphosphonic acid; and hexane-1,2,3,4,5,6-hexaphosphonic acid, respectively, rather than methanediphosphonic acid, in the same molar quantity. Each of these toothpastes effectively retards caries and dental calculus formation without damaging silicate fillings or dental enamel under conditions of normal use.

Several mouthwash compositions illustrating this invention are set forth in the following examples:

| Component | Ex. | IV | V | VI | VII | VIII | IX | X | XI | XII | XIII |
| --- | --- | --- | --- | --- | --- | --- | --- | --- | --- | --- | --- |
| | | | | | | Percent by Weight | | | | | |
| Glycerine | | 10.0 | 10.0 | 10.0 | 10.0 | 10.0 | 10.0 | 10.0 | 10.0 | 10.0 | 10.0 |
| Ethyl alcohol | | 16.5 | 16.5 | 16.5 | 16.5 | 16.5 | 16.5 | 16.5 | 16.5 | 16.5 | 16.5 |
| Tween 80 | | 0.12 | 0.12 | 0.12 | 0.12 | 0.12 | 0.12 | 0.12 | 0.12 | 0.12 | 0.12 |
| Sodium saccharin | | .045 | .045 | .045 | .045 | .045 | .045 | .045 | .045 | 0.45 | .045 |
| Sodium cyclamate | | .075 | .075 | .075 | .075 | .075 | .075 | .075 | .075 | .075 | .075 |
| Flavor | | .088 | .088 | .088 | .088 | .088 | .088 | .088 | .088 | .088 | .088 |

-continued

| Component | Ex. IV | V | VI | VII | VIII | IX | X | XI | XII | XIII |
|---|---|---|---|---|---|---|---|---|---|---|
| Na₂ propane-1,1,3,3-tetraphosphonate | 0.5 | | | | | | | | | |
| Na₂ propane-2,2-diphosphonate | | 1.0 | | | | | | | | |
| (NH₄)₄ ethane-2-carboxy-1,1-diphosphonate | | | 1.5 | | | | | | | |
| Nonane-5,5-diphosphonic acid | | | | 1.75 | | | | | | |
| n-pentane-1,1-diphosphonic acid | | | | | 2.0 | | | | | |
| Ethane-2-phenyl-1,1-diphosphonic acid | | | | | | 2.25 | | | | |
| Pent-4-ene-1-hydroxy-1,1-diphosphonic acid | | | | | | | 2.5 | | | |
| Octadec-9-ene-1-hydroxy-1,1-diphosphonic acid | | | | | | | | 3.0 | | |
| Methanedichlorodiphosphonic acid | | | | | | | | | 3.5 | |
| 3-phenyl-1,1-diphosphonoprop-2-ene | | | | | | | | | | 5.0 |
| Sodium monofluorophosphate | 0.76 | 0.76 | 0.38 | 0.76 | 0.76 | 0.76 | 1.52 | 0.76 | 0.76 | 0.76 |
| Water | | | | | balance | | | | | |
| Mole ratio phosphonate/monofluorophosphate | 0.22 | .75 | 2.0 | 1.2 | 1.6 | 1.6 | 1.0 | 1.4 | 3.1 | 3.4 |

Adjust pH to pH 7.

EXAMPLE XIV

A toothpowder which constitutes yet another embodiment of this invention has the following formulation:

| Component | Percent by Weight |
|---|---|
| Calcium pyrophosphate | 94.00 |
| Sodium lauryl sulfate | 1.30 |
| Sodium saccharin | 0.25 |
| Flavoring | 1.45 |
| Sodium monofluorophosphate | 1.30 |
| Trisodium ethane-1-hydroxy-1,1-diphosphonate | 1.50 |
| Ratio polyphosphonate/fluoride | 0.55 |

When diluted with water and brushed upon the teeth in the conventional manner, this composition has a pH of approximately 7.0. The composition retards the formation of calculus without damaging silicate fillings or dental enamel under conditions of normal use.

The trisodium ethane-1-hydroxy-1,1-diphosphonate employed in the above formulation can be replaced by an equimolar amount of dipotassium ethane-1-amino-1,1-diphosphonate; phenylaminomethanediphosphonic acid; or N,N-dimethylaminomethanediphosphonic acid with substantially equivalent results.

EXAMPLE XV

A prophylaxis paste for use in the dental office for removal of stains and polishing the tooth surface after mechanical removal of calculus is formulated as follows:

| Component | Parts by Weight |
|---|---|
| Composition A | |
| Navajo pumice | 77.1 |
| TiO₂ | 4.0 |
| Glycerine | 17.757 |
| Hydroxyethylcellulose | .222 |
| Sodium saccharin | .326 |
| Composition B | |
| Sodium monofluorophosphate | .450 |
| Methanedibromodiphosphonic acid | .255 |
| Water | 87.00 |
| Ratio polyphosphonate/fluoride | 0.2 |

Immediately prior to use 5.5 gm. of composition A are mixed with composition B to attain the desired texture and adjusted to pH 7.0. The paste is then applied to the tooth surfaces with a rubber prophylactic cup on the conventional manner. This composition inhibits the reformation of calculus without adverse effects on dental enamel as normally used.

The methanedibromodiphosphonic acid of this example can be replaced by an equimolar amount of N-(2-hydroxyethyl) aminomethanediphosphonic acid; bis(triethanolammonium)N-acetylaminomethanediphosphonate; diethanolammonium methanehydroxydiphosphonate; or tris(monoethanolammonium)-nonane-1,1-diphosphonate with comparable results.

EXAMPLE XVI

When in any of the previous examples the following anticalculus agents are substituted, either wholly or in part, for the specified anticalculus agents, substantially equivalent results are obtained in that the formulas provide anticalculus activity without interfering with dental enamel and silicate fillings as normally used: Disodium salt of ethane-1,2-dicarboxy-1,2-diphosphonic acid; dipotassium salt of ethane-1,2-dicarboxy-1,2-dihydroxy-1,2-diphosphonic acid; the di(triethanolammonium) salt of ethane-1,2-dicarboxy-1,2-diphosphonic acid, the disodium salt of ethane-1,2-dicarboxy-1,2-diphosphonic acid; diammonium salt of ethane-1,2-dicarboxy-1,2-diphosphonic acid; triammonium salt of ethane-1,2-dicarboxy-1,2-dihydroxy-1,2-diphosphonic acid; trisodium salt of ethane-1,2-dicarboxy-1-phosphonic acid; hexasodium salt of cyclic tetraphosphonic acid; trisodium salt of methane cyclohexylhydroxydiphosphonic acid; diammonium salt of methanecyclobutylhydroxydiphosphonic acid; triammonium salt of methanecyclononylhydroxydiphosphonic acid; trisodium salt of methanecyclodecylhydroxydiphosphonic acid; methanecycloalkylhydroxydiphosphonic acid; Victamide and mixtures thereof, e.g., 1:1 and 1:1:1 ratios.

EXAMPLE XVII

| Component | Percent by Weight |
| --- | --- |
| Precipitated urea/formaldehyde condensate (abrasive) | 31.00 |
| Sorbitol (70% aqueous solution) | 6.25 |
| Glycerine | 18.00 |
| Sodium coconut alkyl sulfate | 0.40 |
| Sodium coconut monoglyceride sulfonate | 0.75 |
| Sodium carboxymethylcellulose | 1.15 |
| Magnesium aluminum silicates | 0.40 |
| Sodium saccharin | 0.12 |
| Flavoring | 0.95 |
| Methanediphosphonic acid | 1.50 |
| Sodium monofluorophosphate | 3.00 |
| Sodium fluoride | 0.01 |
| Water | balance |
| pH adjusted to 7.5 with 5N NaOH | |

This composition is effective in retarding the formation of dental calculus when used in a conventional manner, and dental enamel and silicate filling materials are not adversely affected thereby. This composition also inhibits caries.

When in the above example the following water-soluble fluoride agents are substituted, either wholly or in part, for the sodium fluoride, substantially equivalent results are obtained in that formulae provide additional anticaries activity:

Stannous fluoride, potassium fluoride, lithium fluoride, cesium fluoride, ammonium fluoride, aluminum fluoride, cupric fluoride, indium fluoride, stannous fluorozirconate, lead fluoride, ferric fluoride, nickel fluoride, paladium fluoride, silver fluoride, zinc fluoride, zirconium fluoride, hexylamine hydrofluoride, laurylamine hydrofluoride, myristylamine hydrofluoride, decanolamine hydrofluoride, octadecenylamine hydrofluoride, myristoxyamine hydrofluoride, diethylaminoethyloctoylamide hydrofluoride, diethanolaminoethyloleylamide hydrofluoride, diethanolaminopropyl-N'-octadecenylamine dihydrofluoride, 1-ethanol-2-hexadecylimidazoline dihydrofluoride, octoylethanolamine hydrofluoride, octyltrimethylammonium fluoride, dodecylethyldimethylammonium fluoride, tetraethylammonium fluoride, dilauryldimethylammonium fluoride, $\Delta^{8,9}$-octadecenylbenzyldimethylammonium fluoride, dioctyldiethylammonium fluoride, cyclohexylcetyldimethylammonium fluoride, furfuryllauryldimethylammonium fluoride, phenoxyethylcetyldimethylammonium fluoride, N:N'-tetramethyl-N:N'-dilaurylethylene-diammonium difluoride, N-cetylpyridinium fluoride, N:N-dilauryl-morpholinium fluoride, N-myristyl-N-ethylmorpholinium fluoride, N-(octylaminocarbonylethyl)-N-benzyl-dimethylammonium fluoride, N-($\beta$-hydroxydodecyl)trimethylammonium fluoride, N-phenyl-N-hexadecyldiethylammonium fluoride, N-cyclohexyl-N-octadecyldimethylammonium fluoride, N-(2-carbomethoxyethyl)-N-benzyldimethylammonium fluoride, N-(2-carbocyclohexoxyethyl)-N-myristyldimethylammonium fluoride, N-(2-carbobenzyloxyethyl)-N-dodecyldimethylammonium fluoride, N-[2-(N:N'-dimethylaminocarbonyl)-ethyl]-N-dodecyldiethylammonium fluoride, N-carboxymethyl-N-eicosyldimethylammonium fluoride, betaine hydrofluoride, sarcosine stannous fluoride, alanine stannous fluoride, glycine potassium fluoride, sarcosine potassium fluoride, glycine hydrofluoride, lysine hydrofluoride, alanine hydrofluoride, betaine zirconium fluoride, and mixtures thereof in, e.g., 1:1 proportions.

EXAMPLE XVIII

| Component | Percent by Weight |
| --- | --- |
| Sorbitol (70% in water) | 20.00 |
| Saccharin, sodium | 0.21 |
| Disodium etidronate (EHDP) | 3.00 |
| NaOH (pellets) | 0.35 |
| Sodium monofluorophosphate | 0.90 |
| Syloid 620 | 11.50 |
| Syloid 63 | 13.00 |
| Flavor oil | 1.00 |
| Sodium alkyl sulfate (28% in water) | 3.12 |
| Glycerin | 10.00 |
| Sodium carboxymethylcellulose | 1.20 |
| Sodium coconut monoglyceride sulfonate | 0.75 |
| Hydrous magnesium aluminum silicate | 0.40 |
| Titanium dioxide | 1.00 |
| Colors | 0.172 |
| Water | balance |

When in the above example, the following abrasives are substituted in the indicated percentages by weight, based on the total composition, for the mixture of Syloid 620 and Syloid 63, substantially equivalent results are obtained in that the formulae provide anticaries and anticalculus activity without interfering with dental enamel and silicate filling materials as normally used: 24% water-insoluble sodium metaphosphate, 34% of any of the specifically named resin abrasives in U.S. Pat. No. 3,070,510; a mixture of 5% water-insoluble sodium metaphosphate, 5% Syloid 65.5% Syloid 73, 2% Syloid 404, and 10% of the abrasive of Example I of Cooley et al.'s U.S. Pat. No. 3,251,800, issued May 17, 1966; a mixture of 10% of the $\beta$-phase calcium pyrophosphate abrasive of Example III of U.S. Pat. No. 3,112,247 and 15% of Syloid 620; 20% of the phenol-formaldehyde resin of Example I of Adams' U.S. Pat. No. 3,357,951, issued Dec. 12, 1967, and 7% Syloid 63; 50% of the phenol-formaldehyde resin of Example I of LaFollette's U.S. Pat. No. 3,357,950, issued Dec. 12, 1967; 20% water-insoluble sodium metaphosphate and 26% Syloid 620; and 45% of the $\beta$-phase calcium pyrophosphate of Example VI of U.S. Pat. No. 3,112,247.

All of the patents and applications mentioned in this application are specifically incorporated by reference.

What is claimed is:

1. An oral composition effective in inhibiting the formation of dental calculus without adversely affecting the tooth structure, dental enamel and silicate filling structure, comprising (1) from about 0.01% to about 10% by weight of an anticalculus agent which would otherwise severely attack the silicate filling structure when used in combination with non-monofluorophosphate water-soluble fluorine sources, said agent being selected from the group consisting of those of the formulae:

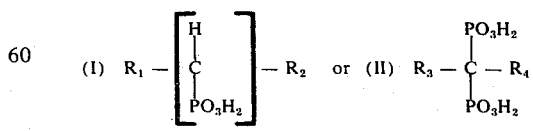

wherein $R_1$ and $R_2$ are either hydrogen or $CH_2OH$; $n$ is an integer of from 3 to 10; $R_3$ is either hydrogen, an alkyl group containing from 1 to about 20 carbon atoms, an alkenyl group containing from 2 to about 20 carbon atoms, a phenyl group, a naphthyl group, a phenylethenyl group, a benzyl group, a halogen atom, an amino group, a dimethylamino group, a diethylamino group, an N-hydroxy-N-ethylamino group, an acetylamino group, —CH$_2$COOH, —CH$_2$PO$_3$H$_2$, —CH(PO$_3$H$_2$) (OH) or —CH$_2$CH(PO$_3$H$_2$)$_2$; and R$_4$ is either hydrogen, a lower alkyl group containing from 1 to about 6 carbon atoms, an amino group, a benzyl group, a halogen atom, a hydroxyl group, —CH$_2$COOH, —CH$_2$PO$_3$H$_2$, or —CH$_2$CH$_2$PO$_3$H$_2$;

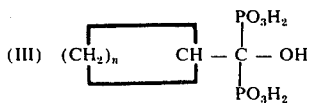

wherein n is an integer from 3 to 9;

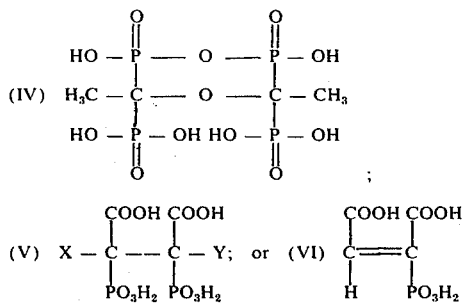

wheren X and Y are each hydrogen or hydroxy; or an orally acceptable salt thereof selected from the group consisting of the alkali metal, ammonium and low molecular weight substituted ammonium salts; or the condensation products of ammonia and phosphorus pentoxide, having the formulae:

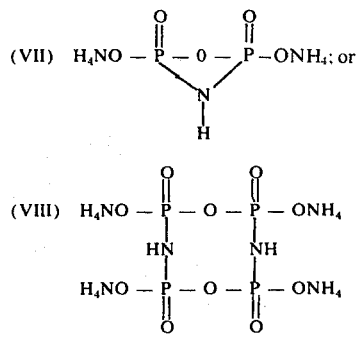

and mixtures thereof; and (2) as the essential fluorine source from about 0.2% to about 8% by weight of an orally acceptable monofluorophosphate, said composition containing no more than 300 ppm of any other water-soluble fluorine source, the pH of the composition being within the range of from about 6.0 to about 7.5.

2. An oral composition in accordance with claim 1 containing from about 0.5% to about 1% by weight of said monofluorophosphate.

3. An oral composition in accordance with claim 1 wherein the monofluorophosphate is sodium monofluorophosphate.

4. An oral composition in accordance with claim 3 wherein the polyphosphonate is ethane-1-hydroxy-1,1-diphosphonic acid or a salt thereof selected from the group consisting of alkali metal, ammonium and low molecular weight substituted ammonium salts.

5. An oral composition in accordance with claim 3 containing from about 0.5% to about 1% by weight of said monofluorophosphate.

6. An oral composition in accordance with claim 1 wherein the polyphosphonate is ethane-1-hydroxy-1,1-diphosphonic acid or a salt thereof selected from the group consisting of alkali metal, ammonium and low molecular weight substituted ammonium salts.

7. An oral composition in accordance with claim 1 wherein the polyphosphonate is methanediphosphonic acid or a salt thereof selected from the group consisting of alkali metal, ammonium and low molecular weight substituted ammonium salts.

8. An oral composition in accordance with claim 1 wherein the polyphosphonate is methanedichlorodiphosphonic acid or a salt thereof selected from the group consisting of alkali metal, ammonium and low molecular weight substituted ammonium salts.

9. An oral composition in accordance with claim 1 wherein the polyphosphonate is methanehydroxydiphosphonic acid or a salt thereof selected from the group consisting of alkali metal, ammonium and low molecular weight substituted ammonium salts.

10. An oral composition in accordance with claim 1 wherein the polyphosphonate is phenylaminomethanediphosphonic acid or a salt thereof selected from the group consisting of alkali metal, ammonium and low molecular weight substituted ammonium salts.

11. An oral composition in accordance with claim 1 wherein the polyphosphonate is N,N-dimethylaminomethanediphosphonic acid or a salt thereof selected from the group consisting of alkali metal, ammonium and low molecular weight substituted ammonium salts.

12. An oral composition in accordance with claim 1 wherein the polyphosphonate is N(2-hydroxyethyl)amino-methanediphosphonic acid or a salt thereof selected from the group consisting of alkali metal, ammonium and low molecular weight substituted ammonium salts.

13. The composition of claim 1 containing from about 0.1% to about 5.0% by weight of the anticalculus agent.

14. The composition of claim 1 containing as an additional ingredient a source of fluoride ions in water in an amount sufficient to give no more than about 300 ppm. of fluoride ion.

15. An oral composition in accordance with claim 1 containing from about 0.5% to about 0.5% to about 95% by weight of an abrasive selected from the group consisting of (1) a predominately β-phase calcium pyrophosphate abrasive having an average particle diameter of from about 3 microns to about 20 microns and having a dentin abrasion value of less than about 700 and a fluoride compatibility greater than about 60%, said calcium pyrophosphate abrasive being derived by uniform heat treatment of a predominantly γ-phase calcium pyrophosphate having a dentin abrasion value of less than 500; (2) a substantialy water-impervious, cross-linked, thermosetting, highly polymerized, synthetic resin abrasive in the form of particles having a mean diameter of from about 5 microns to about 40 microns, said resin being characterized by inertness to ionic ingredients in said composition and having been heat polymerized to a high fluorine ion compatibility; (3) a compatible synthetic, amorphous, porous silica xerogel abrasive having an average particle diameter in the range of from about 2 to about 20 microns; (4) a water-insoluble sodium metaphosphate abrasive having an average particle size diameter of from about 2 to about 20 microns; and (5) mixtures thereof.

16. An oral composition in accordance with claim 15 containing from about 20% to about 60% of said abrasive.

17. An oral composition in accordance with claim 15 wherein the abrasive is a xerogel abrasive.

* * * * *